United States Patent [19]

Dewey et al.

[11] Patent Number: 5,171,242

[45] Date of Patent: Dec. 15, 1992

[54] COMBINATION LENS SYSTEM FOR RETINAL PHOTOCOAGULATOR LASER SYSTEM

[75] Inventors: David A. Dewey, Sunnyvale; Nubar Manoukian, Cupertino, both of Calif.

[73] Assignee: Coherent, Inc., Palo Alto, Calif.

[21] Appl. No.: 604,585

[22] Filed: Oct. 26, 1990

[51] Int. Cl.⁵ .............................. A61N 5/06
[52] U.S. Cl. .............................. 606/4; 606/13; 606/17; 359/823
[58] Field of Search .......................... 606/2-6, 606/10, 11, 17, 18; 128/395-398; 359/684, 694, 823

[56] References Cited

U.S. PATENT DOCUMENTS

| | | |
|---|---|---|
| 3,348,547 | 10/1967 | Kavanagh et al. .......... 606/4 |
| 3,720,213 | 3/1973 | Hobart et al. ............ 128/395 |
| 4,397,310 | 8/1983 | Pomerantzeff ............. 606/4 |
| 4,538,608 | 9/1985 | L'Esperance, Jr. ........ 606/3 |
| 4,576,160 | 3/1986 | Tanaka .................. 606/10 |
| 4,628,416 | 12/1986 | Dewey .................. 362/32 |
| 4,776,335 | 10/1988 | Nakanishi et al. ........ 606/17 |

Primary Examiner—David M. Shay
Attorney, Agent, or Firm—Limbach & Limbach

[57] ABSTRACT

A novel retinal photocoagulator is described, having a laser for generating a beam of laser radiation and a beam delivery system for delivering the laser beam to the surface of the retina. The delivery system includes a lens system for varying the spot size of the beam at the surface of the retina which is operable in two alternate modes over a given range of spot sizes, wherein one of the modes varies the size of the spot while maintaining the beam in a focused condition at the retina, and wherein the other mode varies the size of the spot at the retina by altering it focal point.

18 Claims, 4 Drawing Sheets

COMBINATION LENS SYSTEM FOR RETINAL PHOTOCOAGULATOR LASER SYSTEM

FIELD OF THE INVENTION

The field of this invention is medical laser systems generally and retinal photocoagulator laser systems in particular.

BACKGROUND OF THE INVENTION

Lasers are commonly used today in a variety of medical applications. Lasers have been used dermatologically to destroy skin tumors and remove unwanted skin pigmentation. Physicians have utilized lasers to destroy lithic concretions within bodily cavities, such as kidney stones. Lasers have been used extensively to cut and ablate human tissue, particularly at wavelengths and intensities that result in the coagulation of blood and cauterizing of small vessels contemporaneous with incision making. Called "bloodless" surgery, photocoagulation techniques have found great utility in treating eye disorders, particularly those associated with the retina. Lasers are particularly useful in this regard because of the difficulties in access which internal eye surgery presents and because of the need to prevent blood from entering the vitreous humor of the eye.

Notwithstanding the great advances made in eye surgery using lasers, many problems still remain. One of these is damage to the cornea resulting from laser passage through the cornea on its way to the retina. Although appearing transparent, the cornea and the fluids present between the cornea and the lens do absorb laser energy. In the case of the elderly, cataracts are common resulting in much greater energy absorption than through a normal cornea. Likewise, the subcorneal humors can trigger an immune response which results in a clouding of the fluids and consequent increase in light absorptance.

In conducting any sort of transcorneal laser therapy, energy density of the laser beam as it intersects the cornea must be limited. High energy absorptance by the cornea can result in damage. This problem is compounded by the fact that physicians must use special contact lenses on their patients in order to be able to visualize the placement of the laser beam on the patient's retina. Many of these lens actually increase energy density to the cornea because they have the effect of reducing the diameter of the portion of the laser beam near the cornea compared with what would otherwise be the case. Thus, physicians have sought to minimize the damage potential to the cornea while at the same time maintaining adequate energy densities at the retina necessary for therapy. In many instances, because a focused or parfocal beam is preferred, physicians will chose a lower energy setting and smaller spot size.

An alternative way in which corneal energy densities have been addressed is through the use of a defocused beam, that is, a beam that intersects the retina at a point spaced from the focal plane (i.e., the narrowest portion) of the laser beam. Delivery of a defocused beam of laser radiation to the retina can result in much lower energy densities in the cornea than would be possible if the beam were delivered in a focused mode.

Aside from prevention of damage to the cornea, some physicians find a defocused beam to be more appropriate in certain therapies, particularly where a sharply defined treatment area is not desirable. In these instances, physicians prefer to use a defocused beam.

Generally speaking, known systems are designed to deliver a beam only in a focused or a defocused mode. Some laser systems exist, such as Coherent Model No. 920, which are able to deliver a focused beam for one range of spot sizes and a defocused beam for another range of spot sizes. In the latter range, the spot size is varied by moving the focal plane of the laser beam out of the plane of the retina. No existing devices, however, are able to provide the physician with the option of choosing a focused or a defocused spot for an overlapping range of spot sizes.

Notwithstanding the difficulties associated with corneal damage and the need to use both a focused and defocused beam, prior art laser systems are designed to deliver laser beams in only one mode, focused or unfocused, for a given set of laser beam spot sizes. Thus, there exists a need for a single laser system for treatment of the eye that is capable of delivering a laser beam alternatively in a focused or defocused mode as desired for a range of beam spot sizes.

SUMMARY OF THE INVENTION

The difficulties with prior art laser systems described above are overcome by the present invention which provides a retinal photocoagulator laser system comprising laser means capable of generating a beam of laser radiation having a wavelength and intensity suitable for therapeutic treatment of the retina; laser focusing means coupled to the laser means for adjusting spot size of the beam and for causing the beam to be focused or defocused over a range of spot sizes at a point where the beam intercepts the retina; a source of visible light for illuminating the retina; optical means coupled with the laser focusing means and the visible light source for combining and delivering laser radiation from the laser focusing means and visible light from the visible light source to the retina; and means for magnifying the retina so that the position, spot size and focus of the laser radiation on the retina may be observed.

A distinct advantage of the present invention is that it provides a versatility heretofore unavailable in retinal photocoagulator laser systems. In particular the physician is able to vary spot size in focus over a range of spot sizes but is also able to deliver the beam in a defocused mode over a range of spot sizes that partly or wholly overlaps with the spot sizes which can be generated in a focused mode. This permits the physician to select the wavelength and intensity of laser radiation and contact lens most suited to a particular therapeutic end while at the same time being assured of minimizing the chance of corneal damage due to energy absorption from the laser.

Additional advantages and features of this invention will become apparent from the following detailed description of the preferred embodiment and drawings.

DETAILED DESCRIPTION OF THE INVENTION

Figure 1:
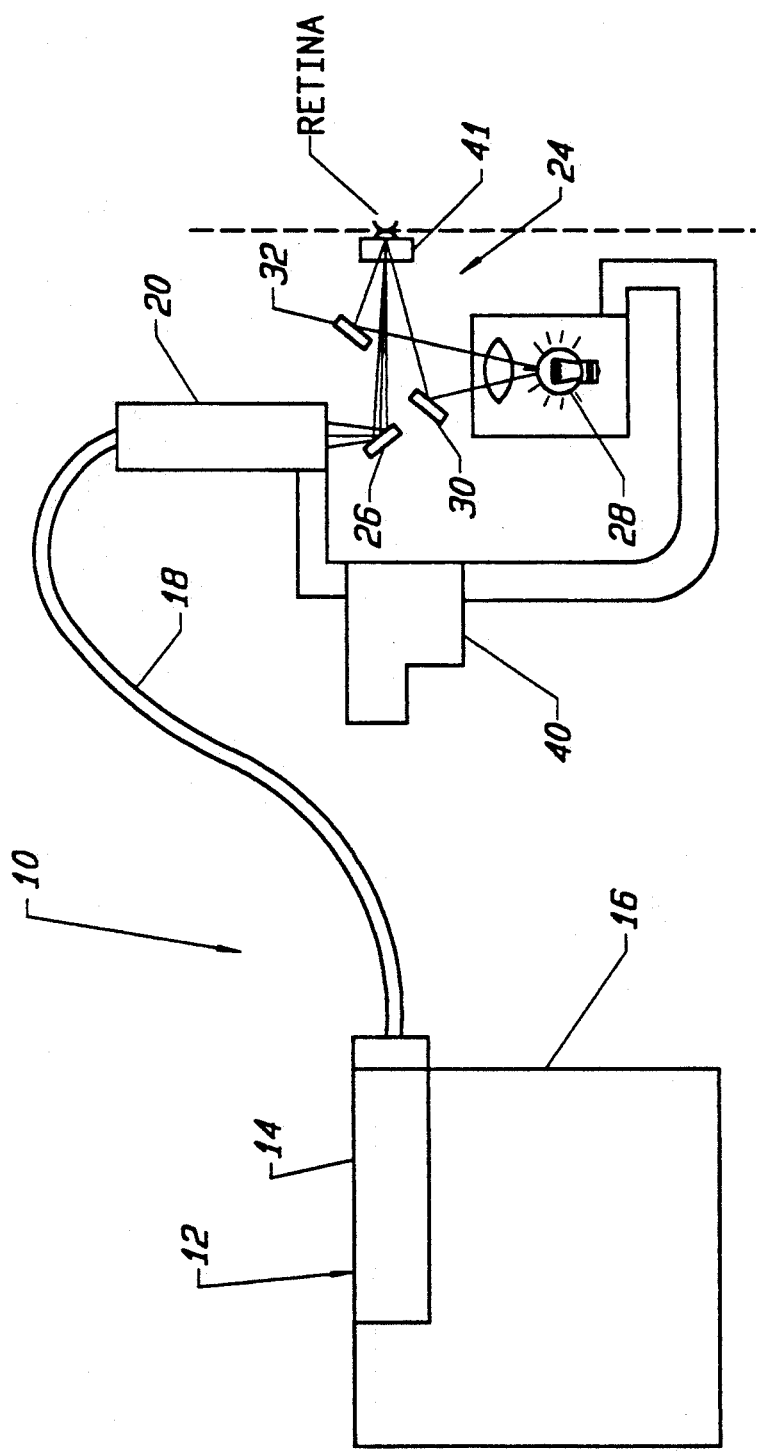
FIG. 1 is a schematic diagram of the retinal photocoagulator laser system of the present invention.

Turning now to FIG. 1, the retinal photocoagulator laser system 10 of the present invention will be described. The laser system 10 is comprised of a laser means 12 for generating a beam of laser radiation having a wavelength and intensity suitable for the desired therapeutic procedure. The laser means 12 is comprised of a suitable laser 14 and a laser control means 16. The laser control means 16 receives power from any suitable outside energy source and delivers it in a controlled fashion to the laser 14. Lasers means suitable for ophthalmological therapies generally and retinal therapies that in particular include Coherent laser consoles which provide both lasers and laser control means and include Coherent's Novus 2000, as well as Coherent's Argon laser console model no. 920 A, Argon-Krypton laser console model no. 920 A/K and a Coherent dye laser console model no. 920 A/DYE.

Laser means 12 is coupled to a laser focusing means 20 by laser transmission means 18. The laser transmission means is generally a cable of optical fiber, although any suitable wave guide capable of efficient transmission of laser radiation at desired wavelengths would be suitable.

Laser focusing means 20 controls the spot size and focus mode of the laser radiation generated by laser means 12. The laser focusing means 20 may be comprised of any system of lenses, mirrors or other construction capable of focusing laser radiation. It is preferred to construct the laser focusing means 20 in the form of a lens system with an adjustable focal length that permits the spot size of the laser radiation at the target to be varied and which also permits the spot to be delivered in a focused or defocused mode for some desired range of spot sizes. The versatility of being able to deliver a variety of spot sizes in a focused or defocused mode ensures that effective doses of laser radiation can be delivered to the target while at the same time maintaining safe energy density levels in corneal tissues.

Optical means 24 for receiving and delivering laser radiation to the retina is coupled to the laser focusing means 20. In the embodiment shown in FIG. 1, the optical means 24 is provided With a first mirror 26 for receiving laser radiation from the laser focusing means 20 and delivering it to the retina. The optical means 24 is also provided with a source 28 of visible light. Light generated by source 28 is received by second and third mirrors 30 and 32 which then reflect the visible light to the retina, thereby providing the illumination necessary for the physician to position the laser radiation.

Magnification means 40 is coupled to optical means 24 opposite the retina to permit the physician to view the retina in order to position properly the laser radiation during therapeutic treatment. A suitable magnification means would be a microscope having magnifying capacity suitable for retinal enlargement. The combination of magnifying means 40 and optical means 24 is frequently referred to collectively as a slit lamp by those skilled in the art. Slit lamps suitable for use in the present invention include the LDS 10a produced by Kowa, Inc. of Japan for Coherent and the Zeiss 30sL, produced by Carl Zeiss Co. of Germany.

In addition to the apparatus just described, it is necessary for the physician to employ a form of a contact lens 41 to make it possible for the physician to focus an image of the retina. Normally the structure of the eye, in particular the action of the lens and cornea of the eye, interferes with the physician's ability to see an image which has been placed on the retina. Thus the physician uses one of a variety of lens systems designed to create an image at a point that is resolvable by mechanical means. The contact lens 41 is placed between the optical means 24 and the retina. Contact lens 41 is positioned so that it is in contact with the cornea through a gel which has been previously placed on the contact lens by the physician. Examples of typical contact lens systems used in conjunction with retinal photocoagulator laser systems include Goldmann 3 Mirror, Krieger, Panfundoscope and Mainster systems.

Figure 2:
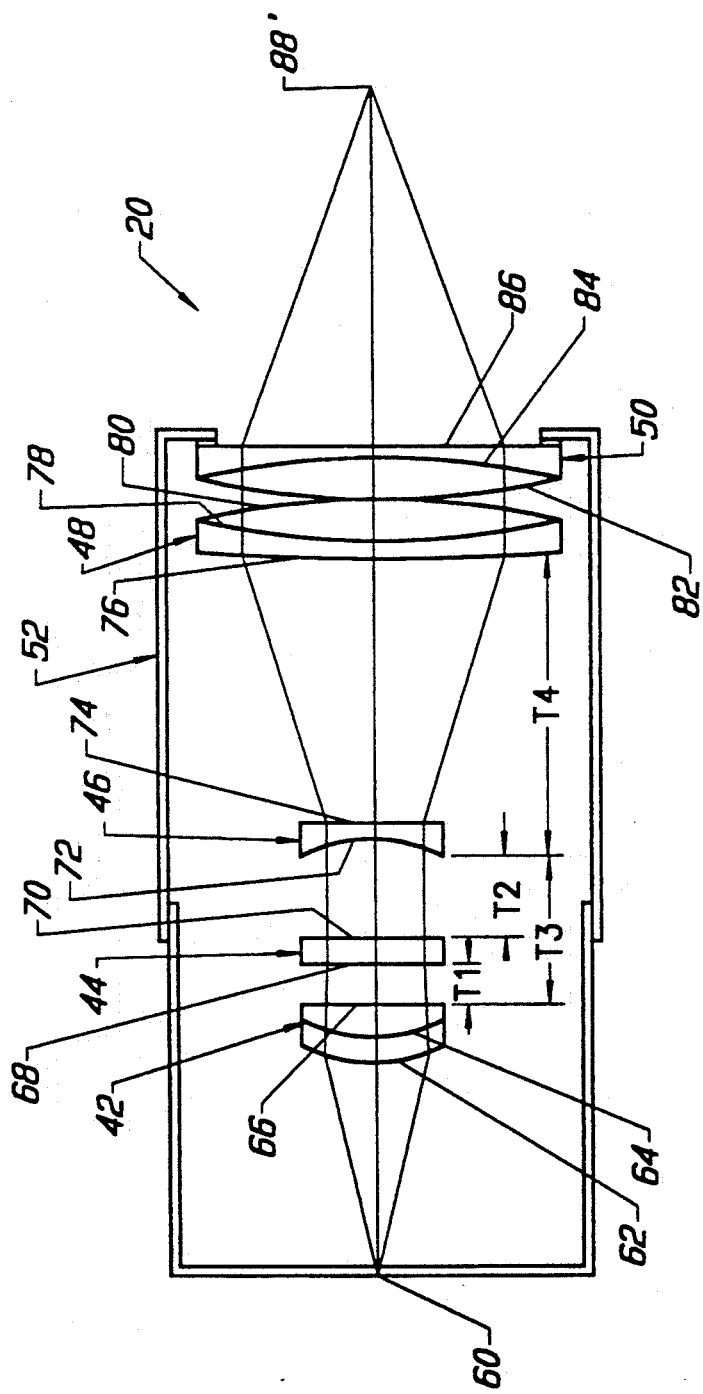
FIG. 2 is a schematic diagram in cross-section of the lens system of the present invention.

Turning now to FIG. 2, the laser focusing means 20 will now be described in greater detail. The laser focusing means of the present invention is comprised of a lens system having a series of lenses some of which are mounted on a cam so that the relative positions of the lenses can be changed in order to achieve a variety of laser beam diameters in both a focused and non-focused mode. In the preferred embodiment as shown in FIG. 2, the lens system 20 is comprised of a first doublet lens 42. A first single lens 44 is placed at a distance $T_1$ from doublet lens 42. A second single lens 46 is next in the series and is position at a distance of $T_2$ from the first single lens 44 and at a distance $T_3$ from the first doublet lens 42. A pair of doublet lens 48 and 50 finish the series and are positioned at a distance of $T_4$ from the second single lens 46. The lenses are mounted in a housing 52 having a cam construction well known in the art so that first and second single lenses 44 and 46 can be moved relative to each other as defined by distance $T_2$ and each relative to the fixed lenses 42, 48, and 50 as defined by distances $T_1$ through $T_4$.

Table I below provides the lens system, lens dimensions and parameters as well as the beam spot size at the lens surface for a beam having a diameter of 55 micrometers at the retina. The surfaces of the lens shown in the first column of the table are labeled in FIG. 2.

TABLE 1

| Surface | Radius of Curvature | Glass Type Mill Spec | Schott Glass Desc. | Distance to Next Surface | Diameter of Beam at Lens Surface | Distance of Surface to Focal Point |
| --- | --- | --- | --- | --- | --- | --- |
| 0 | 0 | 0 | | −.031 | | |
| 60 | 0 | 0 | . | 65.8 | 8.009549E-02 | 1.543574E-04 |
| 62 | 25.26 | 650.394 | BaSF10 | 2.5 | 8.227854 | 152.9218 |
| 64 | 12.18 | 511.605 | K7 | 3.5 | 8.093368 | −2059.486 |
| 66 | −44 | 0 | | 6.649 | 8.106501 | 90.88939 |
| 68 | −66.08 | 740.283 | SF3 | 2 | 7.513588 | 3176.627 |
| 70 | −939.17 | 0 | | 18.473 | 7.509413 | 761.9482 |
| 72 | −33.78 | 626.392 | BaSF1 | 2 | 7.33079 | −93.69418 |
| 74 | 114.17 | 0 | | 83.878 | 7.487256 | −44.2172 |
| 76 | 169.34 | 668.419 | BaSF6 | 2 | 21.68964 | −438.7244 |
| 78 | 44.99 | 640.601 | LAKO1 | 4.7 | 21.7885 | −367.2943 |

TABLE 1-continued

| Surface | Radius of Curvature | Glass Type Mill Spec | Schott Glass Desc. | Distance to Next Surface | Diameter of Beam at Lens Surface | Distance of Surface to Focal Point |
| --- | --- | --- | --- | --- | --- | --- |
| 80 | −103.76 | 0 | | .2 | 22.06731 | 557.5167 |
| 82 | 103.76 | 613.587 | SK4 | 5.3 | 22.05939 | 208.7941 |
| 84 | −41.2 | 668.419 | BaSF6 | 2 | 21.49943 | 255.6317 |
| 86 | −349.79 | 0 | | 117.15 | 21.33124 | 117.1495 |
| 88 | 0 | 0 | | −.0005 | 5.500151E-02 | −5.264282E-04 |

In the particular embodiment of the subject invention, the lens system operates in the focused mode over a range of spot sizes from 50 to 200 microns in diameter. In this range, the energy density through the cornea is generally not a concern. Above 200 microns, a focused beam at the retina will create an energy density in the cornea that can cause problems in certain procedures. Therefore, in the assignees prior device, further increases in spot size were achieved by defocusing the beam.

The subject lens system can also increase the spot size of the beam in the same manner. However, and in accordance with the subject invention, the doctor can select a alternative beam diameter adjustment mode which keeps the beam focused at the retina. The latter option is often selected if the doctor is not concerned with absorption in the cornea and prefers to see a well defined treatment spot.

Figure 3:
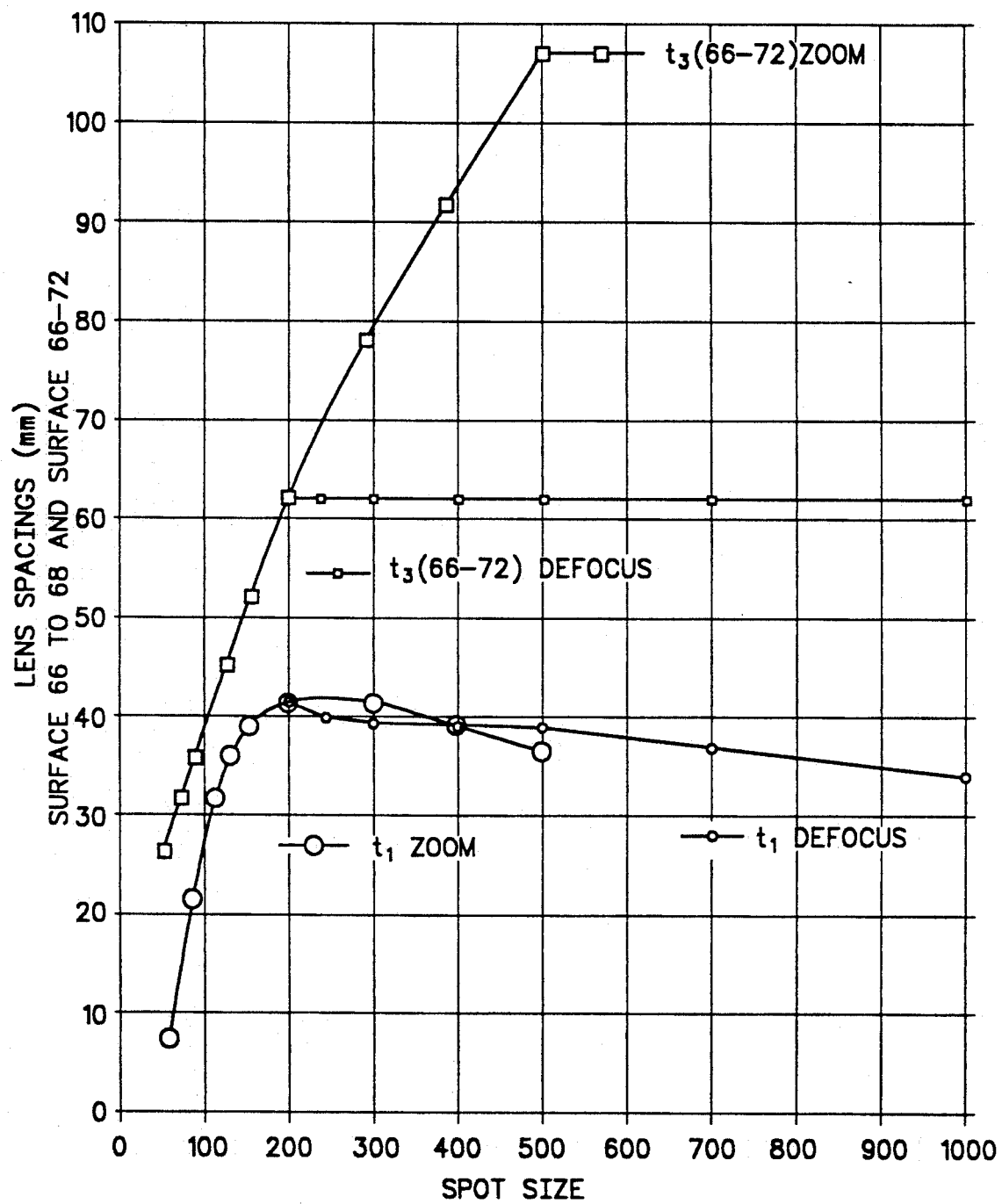
FIG. 3 is a graph of lens spacings within the lens system of the present invention.

FIG. 3 illustrates the movement of lenses 44 and 46, in terms of the spacing between surfaces 66 to 68 ($T_1$) and 66 to 72 ($T_3$) in both of the two operating modes. As can be seen, over the initial spot size range (up to 200 microns), the lenses 44 and 46 move in a manner to keep the spot focused on the retina.

When the beam spot size reaches 200 microns in diameter, the doctor can select one of two alternate modes of beam expansion. In the focused mode, the lenses move in a manner to maintain the beam waist at the retina while expanding the diameter of the beam waist. In the alternate defocus mode, the lenses are moved in a manner to shift the location of the beam waist in order to expand the diameter of the beam at the treatment site.

The selection of the desired mode can be accommodated in hardware by an adjustment ring similar to that which is used to select a macro setting on a conventional zoom lens for a camera. The ability to select either mode over a given range of spot sizes allows the doctor to determine the best approach for a given procedure.

The laser system of the present invention has been designed to deliver a diversity of laser radiation at desired wavelengths and intensities, both in focused and defocused modes, without exceeding energy densities in the cornea which the scientific literature indicates is harmful.

Figure 4:
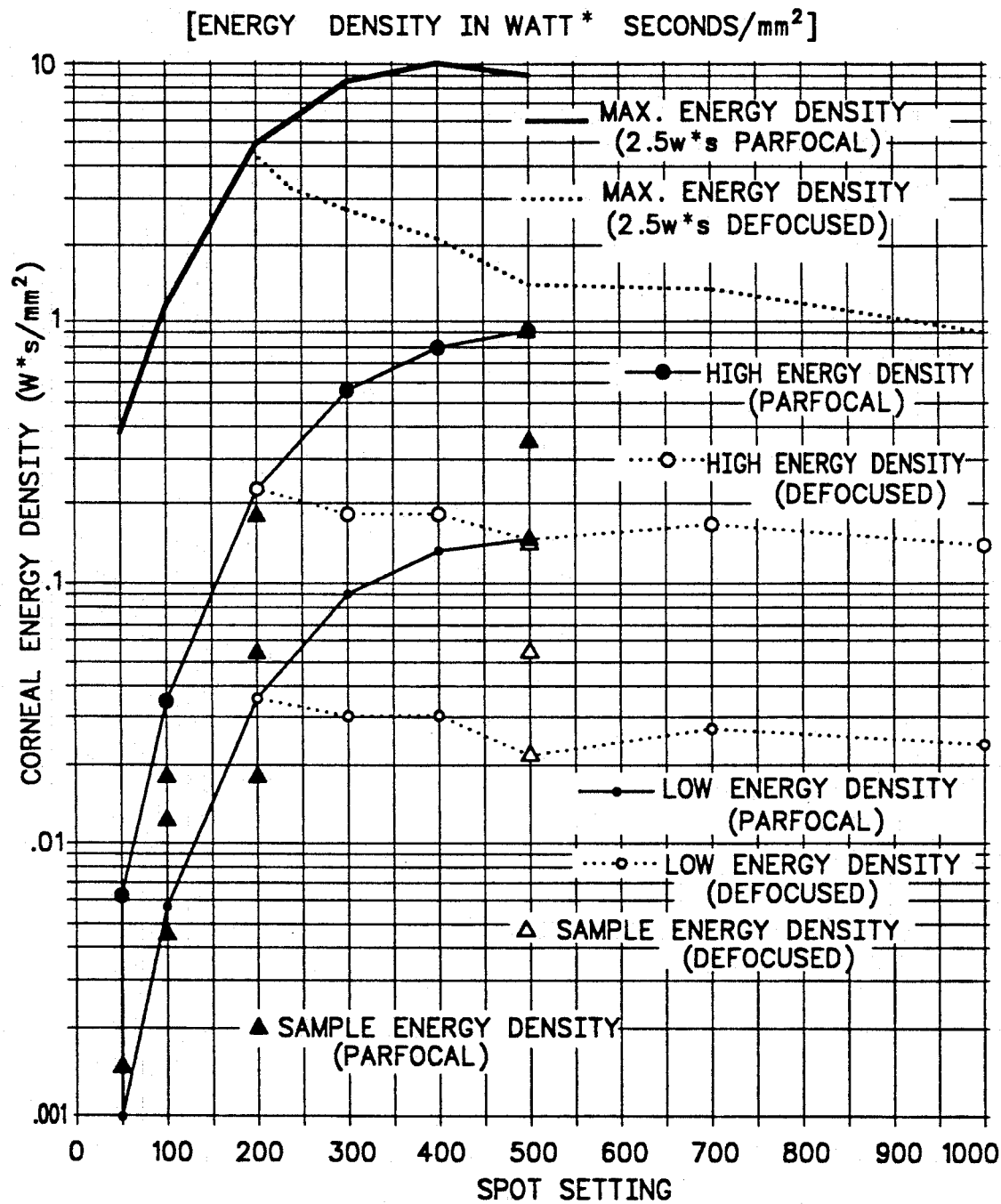
FIG. 4 is a logarithmic graph of corneal energy density relative to spot size in either a focused or defocused mode over a range of given beam intensities with a Goldmann 3 Mirror contact lens.

It is known that energy densities in the cornea in excess of ten watts per square mm can result in some tissue damage to a normal cornea. Thus, computations were made on the laser system of the present invention was tested to ascertain corneal energy densities at a variety of power levels and spots sizes in both a focused and defocused mode. The results are graphically displayed in FIG. 4. As can readily be observed, energy densities are considerably reduced when delivery of the laser radiation is switched to a defocused mode. Further, for typical therapeutic energy levels reported in the literature, corneal energy density is a magnitude or more lower than the 10 w/mm2 threshold at which some damage to the cornea has been observed.

It is now apparent that the apparatus and methods of the present invention for delivering therapeutic laser radiation for a particular spot size in both a focused and defocused mode shows marked improvements over existing retinal photocoagulator laser systems. It is to be understood that although certain preferred embodiments have been disclosed, illustrated and described above, other embodiments are possible without departing from that which is the invention described herein. It is intended therefore that the invention be defined by the claims that follow as well as the equivalents thereof.

We claim:

1. A retinal photocoagulator laser system capable of both parfocal and defocused delivery of laser radiation for therapeutic treatment of a retinal surface comprising:
   a) means for generating a beam of laser radiation having a wavelength and intensity suitable for therapeutic treatment of the retina;
   b) means for delivering the beam of laser radiation to the surface of the retina, said means including an adjustment means for varying spot size of the beam over a given continuous range and for causing the beam to be delivered in either a focused or defocused mode over said given range of spot sizes at the surface of the retina.

2. The laser system of claim 1 wherein the adjustment means includes a plurality of spaced apart lenses through which said laser beam is passed.

3. The laser system of claim 1 wherein the delivering means further comprises a visible light source and an optical means for receiving and delivering laser radiation from the generating means and visible light from the visible light source to the retina.

4. The laser system of claim 1 further comprising magnification means aligned with the retina for viewing the beam of laser radiation on the retina.

5. A laser system as recited in claim 2 wherein the spacing between the lenses is varied to vary the spot size over said range with the spacing change used in the focused mode being different from the spacing change used in the defocused mode.

6. A retinal photocoagulator comprising:
   means for generating a treatment laser beam;
   means for delivering said beam to the surface of the retain, said delivering means including an adjustment means for varying a spot size of the beam at the surface of the retina, said adjustment means being operable in two alternate modes over a given continuous range of spot sizes, wherein one of said modes varies the size of the spot while maintaining the beam in a focused condition at the retina, and wherein an other mode varies the size of the spot at the retina by altering a focal point thereof.

7. The retinal photocoagulator of claim 6 wherein the adjustment means includes a plurality of spaced apart lenses through which said laser treatment beam is passed.

8. The retinal photocoagulator of claim 6 wherein the delivering means further comprises a visible light source and an optical means for receiving and delivering laser radiation from the generating means and visible light from the visible light source to the retina.

9. The retinal photocoagulator of claim 6 further comprising magnification means aligned with the retina for viewing the beam of laser radiation on the retina.

10. A retinal photocoagulator as recited in claim 7 wherein the spacing between the lenses is varied to vary the spot size over said range with the spacing change used in the mode when the beam is maintained in the focused condition being different from the spacing change used in the mode when the beam is maintained in the defocused condition.

11. A retinal photocoagulator laser system capable of both parfocal and defocused delivery of laser radiation for therapeutic treatment of a retina comprising:
   a) a laser capable of generating a beam of laser radiation having a wavelength and intensity suitable for therapeutic treatment of the retina;
   b) laser focusing means coupled to the laser for adjusting spot size of the beam and for causing the beam to be alternatively focused or defocused over a given continuous range of spot sizes at a position where the beam intercepts the retina;
   c) a visible light source;
   d) slit lamp means coupled with the laser focusing means and the visible light source for receiving and delivering laser radiation from the laser focusing means and visible light from the visible light source to the retina and for magnifying the retina so that the position, spot size and focus of the laser radiation on the retina may be observed.

12. A laser system as recited in claim 11 wherein said laser focusing means includes a plurality of spaced apart lenses and wherein the spacing between the lenses is varied to vary the spot size over said range with the spacing change used when the beam is focused being different from the spacing change used when the beam is defocused.

13. A retinal photocoagulator laser system capable of both parfocal and defocused delivery of laser radiation for therapeutic treatment of a retina comprising:
   a) laser means capable of generating a beam of laser radiation having a wavelength and intensity suitable for therapeutic treatment of the retina;
   b) laser focusing means coupled to the laser means for adjusting spot size of the beam over a given continuous range and for causing the beam to be focused or defocused over said given range of spot sizes at a point where the beam intercepts the retina;
   c) a visible light source;
   d) optical means coupled with the laser focusing means and the visible light source for receiving and delivering laser radiation from the laser focusing means and visible light from the visible light source to the retina; and
   e) magnification means aligned with the retina for viewing the beam of laser radiation on the retina.

14. The laser system of claim 13 wherein the laser focusing means includes a plurality of spaced apart lenses through which said laser beam is passed.

15. A retinal photocoagulator as recited in claim 14 wherein the spacing between the lenses is varied to vary the spot size over said range with the spacing change used when the beam is focused being different from the spacing change used when the beam is defocused.

16. A retinal photocoagulator laser system capable of both parfocal and defocused delivery of laser radiation for therapeutic treatment of a retinal surface comprising:
   a) means for generating a beam of laser radiation having a wavelength and intensity suitable for therapeutic treatment of the retina;
   b) adjustment means for varying spot size of the beam at the surface of the retina, the adjustment means being operable in two alternative modes over a given continuous range of spot sizes, wherein one of said modes varies the size of the spot while maintaining the beam in a focused condition at the retina, and wherein an other mode varies the size of the spot at the retina by altering a focal point thereof;
   c) optical means coupled with the adjustment means for generating visible light and for receiving and delivering the beam of laser radiation with the visible light to the retina; and
   d) magnification means aligned with the retina for viewing the beam of laser radiation on the retina.

17. The laser system of claim 16 wherein the adjustment means includes a plurality of spaced apart lenses through which said laser beam is passed.

18. A laser system as recited in claim 17 wherein the spacing between the lenses is varied to vary the spot size over said range with the spacing change used in the mode when the beam is maintained in the focused condition being different from the spacing change used in the mode when the beam is maintained in the defocused condition.

* * * * *